US011224603B2

(12) United States Patent
Knutsen et al.

(10) Patent No.: US 11,224,603 B2
(45) Date of Patent: Jan. 18, 2022

(54) ANTIHISTAMINES IN COMBINATION WITH A RANGE OF SUBSTANCES FOR IMPROVED HEALTH

(71) Applicant: Requis Pharmaceuticals, Inc., West Chester, PA (US)

(72) Inventors: Lars Jacob Stray Knutsen, West Chester, PA (US); Judith Lois Knutsen, Cambridge (GB); Mark A. Pimley, West Chester, PA (US)

(73) Assignee: REQUIS PHARMACEUTICALS, INC., West Chester, PA (US)

( * ) Notice: Subject to any disclaimer, the term of this patent is extended or adjusted under 35 U.S.C. 154(b) by 525 days.

(21) Appl. No.: 15/103,759

(22) PCT Filed: Dec. 13, 2014

(86) PCT No.: PCT/US2014/070185
§ 371 (c)(1),
(2) Date: Jun. 10, 2016

(87) PCT Pub. No.: WO2015/089489
PCT Pub. Date: Jun. 18, 2015

(65) Prior Publication Data
US 2016/0317554 A1    Nov. 3, 2016

Related U.S. Application Data

(60) Provisional application No. 61/915,708, filed on Dec. 13, 2013.

(51) Int. Cl.
| | |
|---|---|
| *A61K 31/57* | (2006.01) |
| *A61K 31/4045* | (2006.01) |
| *A61K 45/06* | (2006.01) |
| *A61K 31/405* | (2006.01) |
| *A61K 31/4168* | (2006.01) |
| *A61K 31/4402* | (2006.01) |
| *A61K 9/48* | (2006.01) |
| *A61K 36/85* | (2006.01) |
| *A61K 36/53* | (2006.01) |
| *A61K 36/708* | (2006.01) |
| *A61K 36/16* | (2006.01) |
| *A61K 31/40* | (2006.01) |
| *A61K 36/71* | (2006.01) |
| *A61K 31/567* | (2006.01) |
| *A61K 36/48* | (2006.01) |
| *A61K 31/455* | (2006.01) |
| *A61K 31/635* | (2006.01) |
| *A61K 33/06* | (2006.01) |

(52) U.S. Cl.
CPC ............ *A61K 31/57* (2013.01); *A61K 9/4825* (2013.01); *A61K 9/4866* (2013.01); *A61K 31/40* (2013.01); *A61K 31/405* (2013.01); *A61K 31/4045* (2013.01); *A61K 31/4168* (2013.01); *A61K 31/4402* (2013.01); *A61K 31/455* (2013.01); *A61K 31/567* (2013.01); *A61K 31/635* (2013.01); *A61K 33/06* (2013.01); *A61K 36/16* (2013.01); *A61K 36/48* (2013.01); *A61K 36/53* (2013.01); *A61K 36/708* (2013.01); *A61K 36/71* (2013.01); *A61K 36/85* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 9,700,548 | B2 * | 7/2017 | Knutsen | A61K 31/56 |
| 2008/0107754 | A1 * | 5/2008 | Luciano | A61K 31/133 |
| | | | | 424/641 |
| 2009/0005351 | A1 * | 1/2009 | Pickar | A61P 13/02 |
| | | | | 514/170 |
| 2012/0302535 | A1 * | 11/2012 | Caufriez | A61K 31/57 |
| | | | | 514/177 |

FOREIGN PATENT DOCUMENTS

| | | | |
|---|---|---|---|
| JP | 2005320254 A | * 11/2005 | |
| WO | WO-2012170883 A1 | * 12/2012 | ............. A61K 31/56 |

* cited by examiner

*Primary Examiner* — Susan Hoffman
(74) *Attorney, Agent, or Firm* — Buchanan Ingersoll & Rooney PC

(57) ABSTRACT

The present invention provides for novel combinations comprising an antihistamine with selected pharmaceutical and nutraceutical agents which alleviate some of the symptoms experienced by menopausal women, optionally combined further with a range of indole-based natural products such as L-tryptophan, 5-hydroxytryptophan and melatonin. These mixtures may be enriched further with pharmaceutically acceptable calcium and magnesium salts as well as selected B vitamins. These combinations have utility in providing a medicament for improving health in mammals, especially for the improvement of menopausal symptoms as welt as sleep in women.

5 Claims, No Drawings

ANTIHISTAMINES IN COMBINATION WITH A RANGE OF SUBSTANCES FOR IMPROVED HEALTH

CROSS REFERENCE TO RELATED APPLICATIONS

This application is the US national application of PCT/US2014/070185, filed on 13 Dec. 2014, which claims priority to U.S. Provisional Application No. 61/915,708, filed on 13 Dec. 2013, the disclosures of which are herein incorporated by reference in its entirety.

FIELD OF THE INVENTION

The present invention is directed to novel combinations of sedating antihistamines with substances that alleviate the symptoms experienced by menopausal women, optionally combined with certain indole-based dietary supplements, and to their use for improving the health of human subjects, including the treatment of menopausal symptoms, improving sleep, inducing restorative sleep function, the treatment of insomnia and other sleep-related problems such as sleep-related breathing conditions and symptoms of circadian rhythm disorders.

BACKGROUND OF INVENTION

Menopause is a stage in a female's life when her ovaries stop producing estrogens as well as progesterone hormones and menstruation ceases. It is a normal part of aging and marks the end of a woman's reproductive years. Menopause typically occurs in a woman's late 40s to early 50s, and there is a strong correlation with sleep problems.

Although hot flushes or flashes and night sweats might seem like minor annoyances to some, these vasomotor symptoms, coupled with other symptoms such as fatigue and exhaustion, mood imbalance, sleep problems, heart discomfort, urogenital problems and joint/muscle problems make many women more susceptible to major health problems during menopause because the loss of estrogen and progesterone can critically impact the brain, the heart, breasts, liver, uterus, bones and all major organ systems.

An estimate from the World Health Organization suggests that 1.1 billion women worldwide will be transitioning into menopause by 2025. It has also been estimated that up to 70% of women experience a range of menopause symptoms, which can occur five to ten years prior to menopause, during the peri-menopause period. The link between menopause and the development of chronic disease has been the subject of much research.

When the ovaries no longer produce adequate amounts of estrogen and progesterone as in menopause), the loss of these hormones can bring about a series of symptoms, including hot flashes (a sudden feeling of warmth that spreads over the body) and sweating. Approximately 75%-85% of menopausal women experience hot flashes, with symptoms lasting for five years or longer. For those experiencing hot flashes or flushes and sweating, sleep difficulties can often arise. According to the National Sleep Foundation in the US, approximately 61% of menopausal women have sleep problems. Issues with sleep can in turn lead to a whole range of other health issues.

Sleep disturbance during menopause is therefore a common and important complaint faced by many women. There are many factors that may play a role in this problem, including vasomotor symptoms, changing hormone levels, circadian rhythm abnormalities, exacerbation of primary insomnia and snoring, mood disorders, co-existent medical conditions as well as lifestyle factors. Treatment strategies can vary from hormonal treatment and medications to lifestyle and behavioral modification (Ameratunga, D; Goldin, J; Hickey, M. Sleep disturbance in menopause. *Internal Medicine Journal*, 2012, 42, 742-747).

Menopause can be considered as one important milestone of increasing occurrence in sleeping problems and a review (Polo-Kantola, P. Sleep and menopause. *Women's health* (London, England), 2007, 3, 99-106) illustrates the effect of menopause on sleep and evaluates different treatment options, especially hormone therapy, in alleviation of symptoms.

One of the functions of sleep is the maintenance, restoration, and repair of the body. Sleep is generally characterized by anabolic activity (including building and remodeling) in muscle, bone, connective tissue, skin, and major organs including the brain. One result of this activity is restoration of function including physical and mental performance such as stamina, energy, and mental alertness. Lack of sleep has consequences for daytime performance and when chronic, for mental health.

Insomnia is a disorder associated with a very stressful life, severe pain and dissatisfaction with one's health, these factors demonstrated the highest association with insomnia (Sutton, D. A., Moldofsky, H. and Badley, E. M. Insomnia and Health Problems in Canadians, *Sleep*, 2001, 24, 665-670). Around 24% of the total Canadian population age 15 and older reported experiencing insomnia. As expected the prevalence of insomnia increased with age, from one fifth of those age 15 to 24 years to slightly more than one third among those 75 years and older. The presence of circulatory, digestive and respiratory disease, allergy, migraine, and rheumatic disorders show the highest associations with insomnia together with pain, stress, and health dissatisfaction. These findings emphasize the importance of recognizing and addressing chronic physical health conditions, pain, and life stress issues in the diagnosis and treatment of insomnia.

An analysis of sleep issues across the life cycle in women (Moline, M. L.; Broeh, L.; Zak, R.; Gross V. Sleep in women across the life cycle from adulthood through menopause. *Sleep Med Rev.* 2003, 7, 155-77) utilized both survey and polysomnographic techniques, and concluded that postpartum sleep issues are nearly universal, but effective and practical countermeasures are still needed. Menopause is associated with insomnia due to several factors including hot flashes, mood disorders and increased sleep-disordered breathing.

A more recent article: (Eichling P. S.; Sahni J. Menopause related sleep disorders. *J. Clin Sleep Med.* 2005, 1, 291-300) concludes that sleep difficulty is one of the hallmarks of menopause. Three sets of sleep disorders are associated with menopause: insomnia/depression, sleep disordered breathing and fibromyalgia, but the primary predictor of disturbed sleep architecture is the presence of vasomotor symptoms. This subset of women has lower sleep efficiency and more sleep complaints; the same group is at higher risk of insomnia and depression. The "domino theory" of sleep disruption leading to insomnia followed by depression has the most scientific support. Estrogen and progesterone themselves may also have antidepressant as well as a direct effect on sleep.

Fibromyalgia has gender, age and probably hormonal associations. Sleep complaints are almost universal in fibromyalgia, since patients have increased CNS levels of the nociceptive neuropeptide substance P and lower serotonin levels resulting in a lower pain threshold to normal stimuli. High substance P and lowered serotonin have significant potential to affect sleep and mood.

Menopausal sleep disruption can exacerbate other pre-existing sleep disorders including restless leg syndrome (RLS) and circadian rhythm disorders. Co-dosing of L-tryptophan, as outlined in the present invention, with the requisite combination of minerals and vitamins, will result in increased CNS levels of serotonin, which raises the pain threshold.

It is clear from these articles that effective drug and nutraceutical treatments for menopause-related sleeplessness and insomnia are still lacking. Antihistamine drugs, i.e. antagonists or inverse agonists of the histamine $H_1$ receptor have been known since the 1940s and 1950s and have been utilized with success as anti-allergy agents. These drugs have proved to be generally safe in low dose and normal use. One of the observed side-effects of many antihistamines is sedation and therefore a range of clinically well-proven antihistamine-based drugs are now available in many territories as over-the-counter (OTC) sleep-aids. They are distinguished from prescription sleep drugs by their milder effect, and their availability in many pharmaceutical markets without a prescription.

Antihistamines which are established for use as anti-allergy agents having a range of sedative effects and therefore have potential use as sleep-aids include Cetirizine, Chlorpheniramine, Clemastine, Desloratadine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine and Triprolidine.

There are a range of drug substances, nutraceuticals and phytonutrients that can have a positive influence on the symptoms of menopause. Examples of these substances are listed as follows:

Tamoxifen and its active derivatives, 4-hydroxytamoxifen and Endoxifen, tibolone, serotonin reuptake inhibitors, clonidine, veralipride, gabapentin, Siberian rhubarb extract, vitamin B6, vitamin B-complex, vitamin D, magnesium, vitamin E, glycine, Ginko Biloba and ginseng, fish oils, eicosapentaenoic acid (EPA) and docosahexaenoic acid (DHA) and other essential fatty acids, borage oil or evening primrose oil (known as sources of gamma linolenic acid), progesterone, 17-hydroxy-6α-methyl-progesterone acetate, estriol, estradiol, a number of phytoestrogens, triterpenoids, phenylpropanoids, ferulic acid, lithium orotate (which can be supplemented with sunflower oil or flaxseed oil to reduce the risk of lithium toxicity), vitex agnus castus (chaste berry), black cohosh (actaea racemosa), dehydroepiandrosterone (DHEA, also known as androstenolone or prasterone, as well as 3β-hydroxyandrost-5-en-17-one or 5-androsten-3β-ol-17-one), soy, Hericium erinaceus, St. John's Wort, red clover and dong quai licorice root.

The tuberous root of the yam is known as a herbal remedy for menopausal symptoms; other preparations with claimed effect may contain isoflavones, such as the isoflavone daidzein metabolite known as equol, or phytohormones, and other plant-based hormones. Acid salts that have been utilized include ammonium succinate, calcium disuccinate, magnesium disuccinate hydrate, zinc difumarate hydrate, tocopherol acetate and monosodium L-glutamate. Additionally, antioxidants such as glutathione, selenium, vitamin C and melatonin may be of therapeutic benefit (Valencia, E.; Marin, A.; Hardy, G. Can antioxidant nutraceuticals benefit the menopause? *Menopause International*, 2002, 8, 98-101).

Extensive research is taking place to confirm the effects of the above substances; see for example an account of a recent conference (Barnes, S.; Kim, H. Cautions and research needs identified at the equol, soy, and menopause research leadership conference. *Journal of Nutrition*, 2010, 140, 1390S-1394S).

Only recently has the peri-menopause become recognized as a time when women are at risk for new onset and recurrence of major depression. Untreated depression at this time not only exacerbates the course of a depressive illness, but also puts women at increased risk for sleep disorders, cardiovascular disease, diabetes, and osteoporosis. Although antidepressant medication is the mainstay of treatment, adjunctive therapy, especially with estrogen replacement, may be indicated in refractory cases, and may speed the onset of antidepressant action (Parry, B. L. Optimal management of perimenopausal depression. *International Journal of Women's Health*, 2010, 2, 143-151). A key risk for depression is through the sequence of stress→insomnia→mood disorders, so new treatments for insomnia with concomitant beneficial effects on menopausal symptoms are particularly necessary.

According to the fourth edition of the Diagnostic and Statistical Manual of Mental Disorders (DSM-IV-TR), insomnia is characterized by one or more of these sleep complaints, which cause clinically significant impairment of daytime functioning:

Difficulty initiating sleep

Difficulty maintaining sleep

Nonrestorative sleep

It is estimated that insomnia is responsible for over $14 billion in direct healthcare costs each year in the United States, and untold billions in lost productivity. Overall, it is believed that the direct and indirect costs attributable to insomnia exceed $100 billion per year in the USA alone (Fullerton D. The economic impact of insomnia in managed care: A clearer picture emerges. *American Journal of Managed Care*, 2006, 12, 246-252). In its initial stages, insomnia occurs when predisposing factors, which include menopausal symptoms, combine with precipitating or triggering factors, typically life stress and anxiety, to bring about issues with falling asleep, mid-nocturnal or early morning awakening or poor sleep quality. Once insomnia begins, perpetuating factors, including a range of largely ineffective compensatory behaviors (e.g. daytime naps, sleeping in on weekends) and negative thoughts can create a vicious cycle, transforming an acute sleep problem into a more chronic one.

Without some form of intervention, negative thoughts about sleep trigger anxiety and create a self-fulfilling prophecy, and this is especially so during menopause. If people believe they will not fall asleep, it is likely they will be tense at bedtime, then as a result can find it difficult to sleep, and pharmacological intervention will be required. Therefore a significant market in non-prescription sleep aids has developed, especially in North America. However, there is a constant need for novel and improved products as existing products have their issues. The successful treatment of menopausal symptoms that disturb sleep is an unmet medical need.

Insomnia, as pointed out above, is associated with a number of health issues. In a review article (Roth, T. Insomnia: Definition, Prevalence, Etiology, and Consequences, *Journal of Clinical Sleep Medicine*, 2007, 3, (suppl.):S7-S10), it is concluded that chronic insomnia is highly prevalent and affects approximately 30% of the general US population. Insomnia impairs cognitive and physical functioning and is associated with a wide range of impaired daytime functions across a number of emotional, social, and physical domains. Compared with good sleepers, people with persistent sleep disturbances are more prone to accidents, have higher rates of work absenteeism, diminished job performance, decreased quality of life, and increased health care utilization. Various risk factors associated with increased prevalence of chronic insomnia include older age, female gender, and co-morbid medical and psychiatric conditions. Approximately 40% of adults with insomnia also have a diagnosable psychiatric disorder—most notably depression. A co-morbid psychiatric disorder such as depression or anxiety may be a consequence of, as well as a risk factor for, disrupted sleep.

Therefore an inability to sleep is often a symptom of stress, and if untreated can lead to severe anxiety and depression. The stressors causing sleep issues can clearly include the physical changes associated with the menopause. A lot of patients self-medicate when suffering from mild and temporary insomnia, and one of the most-used safe treatments is with antihistamines. The subject matter of this invention is that the effect of these sleep-aids be improved further with addition of indole-based dietary supplement(s) including L-tryptophan, 5-hydroxytryptophan (5-HTP) and melatonin to the antihistamine drug formulation. These treatments for disturbed sleep are further combined with substances that treat menopausal symptoms in order to provide comprehensive therapeutic approaches for those suffering for example from hot flashes, fibromyalgia, RLS and a range of related symptoms.

Doxylamine is a preferred member of the ethanolamine class of antihistamine drugs since it possesses an anti-allergy effect in human subjects superior to almost every other antihistamine on the market, with the possible exception of diphenhydramine. It is also the most effective sedative available in general sale the United States, and is seen as more sedating than some prescription hypnotics. One study reputedly found that doxylamine succinate was more effective than the barbiturate phenobarbital for use as a sedative http://www.drugbank.ca/drugs/DB00366).

PCT Int. Appl. WO 2005/063297 relates to pharmaceutical compositions, in particular controlled-release oral dosage forms, comprising a sedative agent, and melatonin or a melatonin analog. In a preferred embodiment, the sedative agent is eszopiclone.

JP 2005320254 claims certain combinations of antihistamines, for example diphenhydramine and melatonin as hypnotics.

PCT Int. Appl. WO 2005/123074 discloses a method is disclosed for the treatment of sleep disorders. The method involves administration of triprolidine, in combination with at least one further active pharmaceutical agent, for enabling an individual to wake refreshed after sleep and the method of treating such an individual with triprolidine. Use of triprolidine, in combination with at least one further active pharmaceutical agent, as active ingredient in the manufacture of a composition for the treatment of sleep disorders is also described.

PCT Int. Appl. WO 2007/020337 relates to the combination of: a short-acting hypnotic agent which is selected from among a modulator of receptors $GABA_A$, a benzodiazepine, a phenothiazine, a melatonin derivative and a melatonin receptor agonist; and a long-acting hypnotic agent which is selected from among a modulator of receptors $GABA_A$, a benzodiazepine, an antagonist of receptors $5HT2_A$ and a calcium ion modulator, for the treatment of sleep disorders.

U.S. Pat. Appl. Publ. US 2002/0004049 describes compositions comprising partially defatted meal from a plant source containing protein-bound tryptophan, preferably squash seeds, and, optionally, a carbohydrate source provided in an amount capable of facilitating transport of in vivo generated tryptophan across the blood brain barrier. Also described are dietary supplements, nutraceuticals, foods and beverages comprising the composition of the invention to induce sleep. The invention further comprises optional use of mannitol in the combination to facilitate BBB transport.

U.S. Pat. Appl. Publ. 2014/0199417 provides combinations comprising a sedating antihistamine and selected indole-based natural products such as L-tryptophan, 5-HTP and melatonin, along With pharmaceutically acceptable calcium and magnesium salts and selected B vitamins. The combinations are useful in providing a medicament for improving sleep in mammals, especially humans.

In a similar manner to many other first-generation antihistamines, diphenhydramine causes strong histamine $H_1$ receptor antagonist-mediated sedation. Diphenhydramine has also been utilized as an anxiolytic agent because of this effect. However, given its pharmacology, diphenhydramine also has anticholinergic properties, leading to the potential side-effects of dry mouth and throat, increased heart rate, pupil dilation, urinary retention, constipation, and, at high doses, hallucinations or delirium. Further side-effects include motor impairment (ataxia), flushed skin, blurred vision at nearpoint owing to lack of accommodation (cycloplegia), abnormal sensitivity to bright light (photophobia), difficulty concentrating, short-term memory loss, visual disturbances, irregular breathing, dizziness, irritability, itchy skin, confusion, decreased body temperature (in general, in the hands and/or feet), erectile dysfunction, and excitability. (see http://www.drug.com/sfx/diphenhydramine-side-effects.html).

The antihistamine diphenhydramine was found to inhibit uptake of the neurotransmitter serotonin, also known as 5-hydroxytryptamine (5-HT). This discovery led to a search for viable antidepressants with similar structures and lowered side-effects, culminating in the invention of fluoxetine (Prozac), a selective serotonin reuptake inhibitor (SSRI). A similar study had previously led to the synthesis of the first SSRI, zimelidine, from brompheniramine, also an antihistamine. This indicates that some antihistamines, including doxylamine, may have a more specific mechanism of action.

The antihistamine promethazine has a strong sedative effect and in some countries is prescribed for insomnia when benzodiazepines are contraindicated. It is available OTC in the UK, Australia, Switzerland and elsewhere, but by prescription only in the USA.

SUMMARY OF THE INVENTION

The present invention is directed to novel combinations of sedating antihistamines and at least one, and preferably two or more dietary supplements, Which can be indole-based, such as tryptophan, 5-HTP, serotonin, N-acetyl-L-5-hydroxy-tryptamine and melatonin, as well substances that treat symptoms of the menopause, and to their use for improving the health of mammals, especially human subjects, including the treatment of insomnia and other sleep-related problems with a variety of causes.

Dietary Supplements: this invention is directed in part to the use of indole-based dietary supplements in combination with antihistamines to provide an enhanced effect in the treatment of temporary or chronic insomnia. Examples of dietary supplements with utility in such combinations are L-tryptophan, 5-HTP, serotonin, N-acetyl-L-5-hydroxytryptamine and melatonin. Melatonin has a number of beneficial effects, particularly in the regulation of sleep. Studies of melatonin have led to the idea that melatonin is an internal sleep "facilitator" in humans, and therefore useful in the treatment of insomnia and the readjustment of circadian rhythms. There is evidence that administration of melatonin is able: (i) to induce sleep when the homeostatic drive to sleep is insufficient; (ii) to inhibit the drive for wakefulness emanating from the circadian pacemaker; and (iii) induce phase shifts in the circadian clock such that the circadian phase of increased sleep propensity occurs at a new, desired time. Therefore, exogenous melatonin can act as soporific agent, a chronohypnotic, and/or a chronobiotic, and role of melatonin in the regulation of sleep, and the use of exogenous melatonin to treat sleep or circadian rhythm disorders is described (Cajochen, C.; Krauchi, K.; Wirz-Justice, A. Role of melatonin in the regulation of human circadian rhythms and sleep. *Journal of Neuroendocrinology*, 2003, 15, 432-437). The use of melatonin in combination with antihistamines will therefore provide an improved sleep-aid, especially in the treatment of circadian rhythm sleep disorders resulting in insomnia and poor sleep quality.

The neurohormone melatonin has other documented health benefits, having been studied in the treatment of cancer, immune disorders, cardiovascular diseases, depression, seasonal affective disorder (SAD), and sexual dysfunction. It possesses potent antioxidant properties.

L-Tryptophan is an essential amino acid, meaning that it cannot be synthesized by the human body and therefore must be part of our diet. Amino acids, including tryptophan, act as building blocks in protein biosynthesis and in addition, tryptophan functions as a biochemical precursor for serotonin, and in turn, melatonin. Serotonin has been implicated in the regulation of sleep, mood, anxiety, appetite, sexual behavior and body temperature. It is produced by biosynthesis in 2 steps from L-tryptophan via the enzymes tryptophan hydroxylase and aromatic amino acid decarboxylase. Serotonin, in turn, can be converted to melatonin, via the action of N-acetyltransferase and 5-hydroxyindole-O-methyltransferase. Niacin is synthesized from tryptophan with kynurenine and quinolinic acids as key biosynthetic intermediates.

In recent years, research has illustrated the utility of L-tryptophan's capacity to influence insomnia. One study found that tryptophan depletion contributed to insomnia; 15 subjects suffering from insomnia were dosed with a drink that depleted tryptophan, and the participants' sleep patterns were studied. It was found that that sleep was significantly disrupted after tryptophan levels were lowered (Riemann, D.; Feige, B.; Hornyak, M.; Koch, S.; Hohagen, F.; Voderholzer, U. The tryptophan depletion test: impact on sleep in primary insomnia—a pilot study. *Psychiatry Research*, 2002, 109, 129-135).

5-HTP is a metabolite of tryptophan. In a further embodiment of this invention one of the indole-based dietary supplement is 5-HTP in combination with antihistamines finds utility in the treatment of disturbed sleep, especially when combined with agents for the improvement of menopausal symptoms.

An alternative pathway of tryptophan metabolism takes place in a series of steps initially involving the enzyme indolamine-2,3-dioxygenase, proceeding via kynurenine derivatives and ultimately leads to Niacin (vitamin $B_3$) (Ruddick, J. P.; Evans, A. K.; Nutt, D. J.; Lightman, S. L.; Rook, G. A.; Lowry, C. A. Tryptophan metabolism in the central nervous system: medical implications. *Expert Rev. Mol. Medicine*, 2006, 8, 1-27). Co-dosing with niacin as part of this novel combination therefore will direct tryptophan metabolism in the direction of 5-HT and its precursor 5-HTP.

Pyridoxine, a $B_6$ vitamin, is involved in production of 5-HT, as the precursor to pyridoxal phosphate, a cofactor for the enzyme aromatic amino acid decarboxylase, responsible for converting 5-HTP into serotonin. When humans are fed diets low in pyridoxine, abnormal metabolism of tryptophan occurs within 5-15 days (Price, J. M. Vitamin $B_6$ and tryptophan metabolism in man. Edited by Yamada, K. Symp. Pyridoxal Enzymes, 3rd., 1968, 213).

Therefore in a further embodiment of this invention, the presence of vitamins such as $B_3$ and $B_6$ that support L-tryptophan metabolism in the direction of 5-HT may be included the novel combination to provide a more effective formulation for sleep improvement in certain groups of women.

The activity of soluble tryptophan hydroxylase from rat brain stem was increased in presence of mM concentrations of calcium, and in addition, the optimal pH for the enzymic activity was shifted from 7.6 to 7.9 following activation by calcium, sodium dodecyl sulphate or trypsin. Under the assay conditions used for measuring tryptophan hydroxylase activity, calcium also stimulated a neutral proteinase (Hamon, M.; Bourgoin, S.; Artaud, F.; Hery, F. Rat brain stem tryptophan hydroxylase: mechanism of activation by calcium. *J. Neurochem* 1977, 28, 811-418). A significant activation of tryptophan hydroxylase (TPH) was achieved by the addition of 1 mM ATP and 10 mM $MgCl_2$ to supernatant prepared from mouse midbrain. The activation produced an increase of enzyme activity by 50-70% above control. The enzyme activation by $Mg^{2+}$-ATP was totally retained after dialysis, thus excluding the possibility of an allosteric effect (Lysz, T. W.; Sze, P. Y. Activation of brain tryptophan hydroxylase by a phosphorylating system. *J. Neurosci. Res.*, 1978, 3, 411-418).

In a further embodiment of this invention, minerals such as calcium and magnesium that support L-tryptophan metabolism in the direction of 5-HT may be included the novel combination to provide a more effective formulation for sleep improvement in mammals.

In a further embodiment of this invention, compositions of antihistamines, indole-based dietary supplements and substances influencing peri- and post-menopausal symptoms are claimed which have utility in the treatment of jet lag, also known as jet lag disorder.

DETAILED DESCRIPTION OF THE INVENTION

The present invention is directed to novel combinations of sedating antihistamines and certain indole-based dietary supplements, with substances that alleviate the symptoms experienced by menopausal women and to their use for improving the health of human subjects, including the treatment of insomnia and other sleep-related problems such as issues with circadian rhythm and Jet Lag Disorder (JLD). A further embodiment of the invention is for specific combinations of a pharmacologically active and bioavailable antihistamine ($H_1$ receptor antagonist), a melatonin component and a tryptophan component.

A further embodiment of the invention is for specific combinations of a pharmacologically active and bioavailable antihistamine ($H_1$ receptor antagonist), with substances that alleviate the symptoms experienced by menopausal women, optionally with a melatonin component and a tryptophan component, optionally combined with one or more vitamins such as $B_3$ and $B_6$, and one or more minerals such as calcium and magnesium. These compositions, and methods of use thereof, are useful for to provide a more effective formulation for sleep improvement, thereby alleviating the symptoms experienced by menopausal women and more directly inducing restorative sleep and its benefits.

Various documents including, for example, publications and patents, are recited throughout this disclosure. All such documents are hereby incorporated by reference. Trade names for products or components including various ingredients may be referenced herein. The inventors herein do not intend to be limited by materials under a certain trade name.

In the description of the invention various embodiments or individual features are disclosed. As will be apparent to the ordinarily skilled practitioner, all combinations of such embodiments and features are possible and can result in preferred executions of the present invention. The compositions herein may comprise, consist essentially of, or consist of any of the elements as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

With respect to dosing preferences, dosage levels are developed based on typical human subjects (e.g. a 70 kg subject). If the present composition is used in other mammals or in various human subjects, it may be necessary to modify the dosage. Modification of dosages based on the needs of the subject is well within the skill of the ordinary artisan. It is therefore understood that these dosage ranges are by way of example only, and that daily administration can be adjusted depending on various factors. The specific dosage of the compound to be administered, and the duration of treatment are interdependent. The dosage and treatment regimen will also depend upon such factors as the specific compound used, the treatment indication, the efficacy of the compound, the personal attributes of the subject (such as, for example, weight, age, gender, and medical condition of the subject), and compliance with the treatment regimen.

In a further embodiment of this invention, novel compositions of antihistamines, indole-based dietary supplements such as tryptophan, 5-HTP, melatonin along with substances that alleviate the symptoms experienced by menopausal women, further in combination with niacin (also known as vitamin $B_3$, nicotinic acid or vitamin PP) are claimed for the treatment of insomnia and other sleep-related problems such as issues with circadian rhythm and jet lag. Co-dosing of vitamins, for example niacin, assists in the metabolism of tryptophan to serotonin in human subjects.

In a further embodiment of this invention, novel compositions of antihistamines, indole-based dietary supplements such as tryptophan, 5-HTP and melatonin along with substances that alleviate the symptoms experienced by menopausal women in combination with vitamin $B_6$ are claimed for the treatment of insomnia and other sleep-related problems such as issues with circadian rhythm and jet lag. Co-dosing of vitamins, for example $B_6$, assists in the metabolism of tryptophan to serotonin in human subjects.

In a further embodiment of this invention, novel compositions of antihistamines, indole-based dietary supplements such as tryptophan, 5-HTP and melatonin along with substances that alleviate the symptoms experienced by menopausal women in combination with pharmaceutically acceptable calcium salts and substance(s) with utility in the treatment of menopausal symptoms, are claimed for the treatment of insomnia related to and derived from menopausal symptoms and other sleep-related problems such as issues with circadian rhythm and jet lag. Representative pharmaceutically acceptable calcium salts are calcium hydrochloride, calcium tartrate, calcium maleate, calcium citrate, calcium phosphate, calcium acetate, calcium lactate calcium fumarate, calcium sulfate, calcium bromide, calcium mesylate, calcium palmoate, calcium iodide, calcium nitrate and calcium methylsulfate.

These novel combinations of sedating antihistamines and indole-based dietary supplements along with substances that alleviate the symptoms experienced by menopausal women together with calcium salts have utility in the treatment of insomnia and other sleep-related problems such as issues with circadian rhythm, shift work disorder and jet lag. It is known that calcium stimulates the metabolism of tryptophan and the presence of calcium salts will bring about more rapid formation of serotonin (Boadle-Biber, M. C. Effect of calcium on tryptophan hydroxylase from rat hind brain. *Biochem. Pharmacol.*, 1975, 24, 1455-1460).

In a further embodiment of this invention, compositions of antihistamines and indole-based dietary supplements with optional addition of niacin and calcium salts combined with substance(s) having utility in the treatment of menopausal symptoms, are provided in a liquid form as a drink to be taken at bedtime to improve sleep. In a preferred embodiment the liquid formulation can be ingested either before or during or after a long aircraft flight to aid rest and sleep as well as treating the symptoms of jet lag including issues with circadian rhythm. The presence of vitamins, sugars, sources of complex carbohydrates and other ingredients and formulations are also added, familiar to those skilled in the art of preparing beverages.

Methods of Use

The methods of the present invention comprise orally administering (i.e., through ingestion) a composition of the present invention to a mammal, preferably a human, to provide various health benefits, including treatment of insomnia and inducing restorative sleep function and combinations thereof. The compositions of the present invention are most preferably ingested by consumers primarily desiring restorative sleep function while taking advantage of the restorative actions of the mammalian body during rest sleep. The compositions of this invention may also be ingested as a supplement to normal dietetic requirements.

Frequency of administration is not limited. However, such administration for treatment of insomnia is typically at least once weekly, more preferably at least 3 times weekly, and most preferably at least once daily around bedtime. As used herein, "restorative sleep function" refers to alleviation of any circadian rhythm phase-shifting effect, jet lag, winter depression, shift work-related desynchronies, sleep phase disorders, and other sleep disorders, improvement in sleep quality, improvement of sleep duration, and combinations thereof.

As used herein, the term "orally administering" with respect to the mammal (preferably, human) means that the mammal ingests or is directed to ingest (preferably, for the purpose of providing one or more of the health benefits described herein) one or more compositions of the present invention. In one embodiment, the composition is formulated as a tablet, capsule, food or beverage composition. Wherein the mammal is directed to ingest one or more of the compositions, such direction may be that which instructs and/or informs the user that use of the composition may and/or will provide one or more general health and/or general physiological benefits including, but not limited to, restorative sleep function.

The following are non-limiting examples of Methods which can be utilized to provide tablet formulations of the novel combinations which are useful in providing a medicament for improving sleep in mammals, especially humans.

Method A

A capsule formulation is prepared for use in treating sleep disorders in mammals comprising 0.001 g to 0.05 g of a suitable sedating antihistamine, for example doxylamine as its pharmaceutically acceptable salt, for example its succinate salt form, between 0.0025 g and 0.5 g of progesterone, 0.0001 g to 0.01 g of melatonin, 0.001 g to 1.0 g of L-tryptophan, 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shin work disorder and jet lag.

Method B

A capsule formulation is prepared for use in treating sleep disorders in mammals comprising 0.001 g to 0.05 g of a suitable sedating antihistamine, for example doxylamine as its pharmaceutically acceptable salt, for example its succinate salt form, 50 mcg to 0.015 g estriol, 0.0001 g to 0.01 g of melatonin, 0.001 g to 1.0 g of L-tryptophan, 0.01 g to 0.05 g of niacin and 0.001 g to 0.01 g of pyridoxine. Suitable excipients for this tablet formulation include dicalcium phosphate, calcium citrate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method C

A capsule formulation is prepared for use in treating sleep disorders in mammals comprising 0.001 g to 0.05 g of a suitable sedating antihistamine, for example doxylamine as its pharmaceutically acceptable salt, for example its succinate salt form, 10 mcg to 0.015 g of estradiol, 0.0001 g to 0.01 g of melatonin, 0.001 g to 1.0 g of L-tryptophan, 0.01 g to 0.05 g of niacin and 0.01 g to 0.1 g of theanine. Suitable excipients for this tablet formulation include dicalcium phosphate, calcium citrate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method D

A capsule formulation is prepared for use in treating sleep disorders in mammals comprising 0.005 g to 0.01 g of a suitable sedating antihistamine, for example diphenhydramine as its pharmaceutically acceptable salt, for example its hydrochloride or citrate salt form, 0.0005 g to 0.5 g black cohosh, 10 mcg to 0.015 g estrone, 0.0001 g to 0.01 g of melatonin, 0.001 g to 1.0 g of L-tryptophan, 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep-related problems such as issues with circadian rhythm, shift work disorder and jet lag.

Method E

A capsule formulation is prepared for use in treating sleep disorders in mammals comprising 0.05 g to 0.1 g of a suitable sedating antihistamine, for example promethazine as its pharmaceutically acceptable salt, for example its hydrochloride salt form, 0.01 g to 0.25 g red clover, 0.25 to 5 g Valerian root (crude herb), 0.0001 g to 0.01 g of melatonin, 0.001 g to 1.0 g of L-tryptophan, 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep related problems such as issues with circadian rhythm, shift work disorder and jet lag.

Method F

A capsule formulation is prepared for use in treating sleep disorders comprising 0.0001 g to 0.01 g of melatonin, 0.001 g to 1.0 g of L-tryptophan, 0.05 g 0.5 g DHEA, 0.01 g to 0.25 g red clover, 0.25 to 5.0 g Valerian root (crude herb), 0.01 g to 0.05 g of niacin, 0.001 g to 0.01 g of pyridoxine, 0.01 to 1.0 g of a suitable mineral salt of calcium, for example calcium citrate and 0.005 to 0.5 g of a magnesium compound such as magnesium oxide. Suitable excipients for this tablet formulation include dicalcium phosphate, acceptable dyes such as FD&C Blue #1 aluminum lake, magnesium stearate, microcrystalline cellulose and sodium starch glycolate. The tablet is dosed to human subjects in order to improving their health, especially in the treatment of sleep problems, including inducing restorative sleep function, in the treatment of insomnia and other sleep related problems such as issues with circadian rhythm, shift work disorder and jet lag.

Method G

A composition of doxylamine succinate (0.025 g), the indole-based dietary supplements L-tryptophan (0.5 g) melatonin (0.003 g) were dissolved in pasteurized milk (250 mL) or a suitable fruit juice such as mango juice (250 mL), or a combination of juices, and Evening Primrose Oil (0.5 g), Siberian rhubarb extract (0.5 g), vitamin B6 (0.010 g), vitamin E (0.010 g) and glycine (1.0 g) were introduced. Niacin (0.25 g) and calcium citrate (2.5 g) were added, followed by a source of carbohydrate, with vitamin C (0.5 g) and a suitable approved flavoring. This scaleable formulation is in a beverage form as a drink, preferably to be taken at bedtime to improve sleep, or before, during or after a long aircraft flight to aid rest and sleep as well as treating the symptoms of jet lag, including disorders of circadian rhythm.

The following are non-limiting examples of the present compositions which are prepared utilizing conventional methods. The following examples are provided to illustrate the invention and are not intended to limit the scope thereof in any manner.

EXAMPLE 1

Doxylamine succinate (0.80 g), progesterone (5.0 g), L-tryptophan (32.50 g), melatonin (0.15 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure.

Utilizing a Jaansun® Capsule Machine 100, the mixture was carefully placed into "0" Clear Locking gelatin capsules (part # #30-1988-5000, obtained from pCCA USA, 9901 S. Wilcrest Drive, Houston, Tex. 77099-5132) as described below, following the manufacturer's instructions closely.

The loader filled with empty capsules was placed on top of the separator plate so that it could slide freely from left to right. The loader was positioned on the blue rails and slid to the left or right till it stopped against one set of the blue posts. The White plate was then gently pushed into the spring block, and the capsules were allowed to drop through the loader plates with the lid end up. The loader was lifted up and off the capsule machine.

One of the retainer knobs was grasped and the separator plate was shaken to drop the capsules into the machine, ensuring that the capsules were sitting in the capsule machine so that the capsule tops could not rise above the blue metal ledge located just beneath the retainer knobs. Once the capsules had dropped into the machine, the capsules were gently tapped to ensure they were all at the required height; the procedure was then repeated for the remaining 50 capsules.

The loader was lifted up and off of the capsule machine, and all capsules were tapped gently to ensure they were sitting level in the capsule machine. The retainer plate was then placed on top of the separator plate with the beveled edges facing up, parallel to each set of retaining knobs. Each retainer knob was turned so that approximately ⅓ of the knob was covering the plate, and both pinch knobs were hand-tightened at the same time. The separator plate was then lifted up and off of the machine, and checked for capsule bases. Before setting the separator plate aside, it was ensured that the black retaining knobs were facing upwards.

The black pinch knobs were loosened and the capsules were allowed to drop down into the capsule machine so they were sitting flush with the top of the white pinch plate. The black pinch knobs were lightly tightened to hold the capsule bases in place during the filling process; the optional powder dam was placed on the top of the machine and the requisite clips applied over the powder dam and the short notch under the machine.

The thoroughly-mixed ingredients, as described above, were placed in powder form in the center of the machine and spread evenly over the top of the white pinch plate with a powder scraper. The machine was gently tapped in order to move the powders back and forth on the white pinch plate. The powders were tamped with a tamper to push air out of, and powder into the capsules, then the powder was redistributed over the capsules with a scraper as needed, checking for fill uniformity. This tapping, tamping, and scraping process was repeated until all the powder was neatly packed into the capsules.

Once it appeared that the majority of the powder has been packed into the capsules, the clips and powder dam were removed, and the tamper was used to check for capsule fill uniformity. If one end of tamper was sitting higher than the other end, the powder distribution was evened out using the tamper prongs as a scoop or manipulated with a plastic scraper/spatula if needed. The capsules were now ready to be reassembled by the following procedure: the separator plate was placed on the machine with the notches to the front door, and both pinch knobs were loosened, but with the retainer knobs holding the retainer plate in place. The depth plate was gently bounced while gradually applying pressure to raise the depth plate up. Pressure was applied to both the front and back of the plates to bring all the capsules back together.

The separator plate was then lifted up, and checked underneath to ensure that all capsule bases had been reattached to the lids; and the retainer knobs were checked again to ensure that they are still holding the retainer plate in place. The separator plate was turned over and each capsule locked by gently pressing down on each one individually. The retainer plate was removed by rotating the retainer knobs and lifting the plate up and off the separator plate. The capsules were removed from the separator plate by turning the plate over and guiding the capsules into a towel, then the four corners of the towel were brought together and the capsules were shaken, thereby cleaning the capsules and loading the capsule lids.

The batch of 100 capsules was then available for clinical evaluation, in a typical daily dose of 2 capsules at bedtime in subjects suffering from sleep problems related to menopausal symptoms, especially subjects who take dietary supplements ensuring healthy and adequate levels of the minerals calcium and magnesium.

EXAMPLE 2

Doxylamine succinate (0.80 g), DHEA (4.0 g), L-tryptophan (32.50 g), melatonin (0.15 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure as described in Example 1.

EXAMPLE 3

Doxylamine succinate (0.80 g), tibolone (2.5 g), L-tryptophan (32.50 g), melatonin (0.15 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure as described in Example 1.

EXAMPLE 4

Doxylamine succinate (0.80 g), veralipride (7.0 g), L-tryptophan (32.50 g), melatonin (0.15 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure as described in Example 1.

EXAMPLE 5

Doxylamine succinate (0.80 g), clonidine (10.0 g), L-tryptophan (32.50 g), melatonin (0.15 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure as described in Example 1.

EXAMPLE 6

Doxylamine succinate (0.80 g), 17-hydroxy-6α-methyl-progesterone acetate (0.25 g), L-tryptophan (32.50 g), melatonin (0.15 g) were all weighed on a Ohaus Explorer scale and combined with microcrystalline cellulose NF105 (Avicel™) (1.0 g). The ingredients were mixed thoroughly in a sterilized plastic container and the mixture was now ready for the capsule preparation procedure as described in Example 1.

A method for assessing the effects of drugs on sleep time as well as differences in rapid eye-movement (REM) sleep, slow-wave sleep and wakefulness is illustrated in Example 7.

EXAMPLE 7

Twenty-five male Sprague-Dawley rats (300-350 g at the time of the surgery) were anesthetized with 2.5-3.0% halothane (Halocarbon Laboratories, and surgically implanted for sleep recordings. Two screw electrodes were placed in the parietal bone over the hippocampus (P=4.0; L=3.0), to record the electroencephalogram (EEG). Two wire electrodes were placed in the external and internal canthus of the orbit to record eye movements (EOG). Postural tone (EMG) was recorded through two wire electrodes inserted into the neck musculature. A stainless steel cannula (23 gauge) was stereotaxically implanted into the lateral ventricle. Rats were individually housed and the light-dark cycle was controlled (12:12, lights on at 06.30 h)

One week after the surgery, rats were habituated to the recording conditions for at least 2 days. Rats were recorded in a small cage (16×10×10") placed inside of an environmental chamber (35×34×9"). Once the habituation period was completed, rats were divided into five groups (n=5). Each group was challenged with an intraventricular (ICV) administration of a solution of the desired proportions doxylamine succinate/progesterone/L-tryptophan/melatonin or ethanol (EtOH, J. T. Baker). Control animals received 10 □l of saline. Rats were continuously recorded for 8 h after the ICV injection (1000-1800 h). In addition, rats were observed for changes in spontaneous behavior through a one-way window. These methods are described in more detail in Prospero-Garcia, O.; Criado J. R. and Henricksen, S. J., A method for investigating sleep: Pharmacology of Ethanol and Glutamate Antagonists on Rodent Sleep: A Comparative Study. *Pharmacology Biochemistry and Behavior,* 1994, 49, 413-416.

Acid addition salts of the antihistamine and optional melatonin, 5-HTP and tryptophan combinations and other agents employed in the invention can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic and related organic or inorganic acids.

The antihistamine and optional melatonin, 5-HTP and tryptophan combinations and their pharmaceutically acceptable salts, may be administered alone or in combination with pharmaceutically acceptable carriers, in either single or multiple doses. Suitable pharmaceutical carriers include inert solid diluents or fillers, sterile aqueous solutions, oils (e.g. peanut oil, sesame oil) and various organic solvents. Enterically coated tablets are a preferred formulation when 5-HTP is utilized as one of the indole-based dietary supplements. The pharmaceutical compositions formed by combining the antihistamine and optional melatonin, 5-HTP and tryptophan combinations and pharmaceutically acceptable carriers can be readily administered in a variety of dosage forms such as tablets, powders, lozenges, emulsions, oil soft gels, syrups, injectable solutions and the like. These pharmaceutical compositions can, if desired, contain additional ingredients such as flavorings, binders, excipients, taste-masking agents and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia.

Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions, elixirs or beverages are desired for oral administration, the essential active ingredient therein may be combined with a large range of various sweetening or flavoring agents, coloring matter or dyes and, if desired, emulsifying or suspending agents, together with diluents such as water, ethanol, propylene glycol, glycerin and combinations thereof.

For parenteral administration, solutions containing the antihistamine and optional melatonin, tryptophan and 5-HTP combinations or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for the antihistamine, melatonin, 5-HTP and tryptophan combinations employed in the methods of this invention will depend on the intended route of administration and factors such as the age and weight of the patient. The dosages will also depend on the particular condition to be treated and will generally range from about 0.1 to about 300 mg/kg body weight of the patient per day, with administration carried out in single or divided dosages.

The invention claimed is:

1. A pharmaceutical composition for the induction of restorative sleep function consisting of the active ingredients 0.001 g to 0.05 g of doxylamine or a pharmaceutically acceptable salt thereof, a dietary supplement, and 0.0025 g and 0.5 g of 17-hydroxy-6 alpha-methyl-progesterone acetate;

wherein said pharmaceutical composition is formulated as a tablet or capsule and further comprises the inactive ingredients selected from a binder, a lubricating agent, and a filler.

2. The pharmaceutical composition according to claim 1 wherein the dietary supplement is an indole-based compound.

3. The pharmaceutical composition of claim 2 wherein the indole-based compound is L-tryptophan or a derivative of L-tryptophan.

4. The pharmaceutical composition according to claim 2 wherein the dietary supplement further includes at least one vitamin and pharmaceutically acceptable minerals to enhance the effect of an indole-based compound(s).

5. The pharmaceutical composition according to claim 1 wherein the dietary supplement includes pharmaceutically acceptable calcium salts, magnesium salts, and at least one pyridine-based vitamin.

\* \* \* \* \*